(12) United States Patent
Goutayer et al.

(10) Patent No.: US 9,072,775 B2
(45) Date of Patent: Jul. 7, 2015

(54) FLUORESCENT EMULSIONS FOR OPTICAL IMAGING

(76) Inventors: Mathieu Goutayer, St Malo (FR); Isabelle Texier-Nogues, Grenoble (FR); Jacques Fattaccioli, Ajaccio (FR); Jérôme Bibette, Paris (FR); Anabela Da Silva, Grenoble (FR)

(*) Notice: Subject to any disclaimer, the term of this patent is extended or adjusted under 35 U.S.C. 154(b) by 897 days.

(21) Appl. No.: 12/527,314

(22) PCT Filed: Feb. 14, 2008

(86) PCT No.: PCT/FR2008/000196
§ 371 (c)(1),
(2), (4) Date: Nov. 16, 2009

(87) PCT Pub. No.: WO2008/125747
PCT Pub. Date: Oct. 23, 2008

(65) Prior Publication Data
US 2010/0284932 A1 Nov. 11, 2010

(30) Foreign Application Priority Data
Feb. 14, 2007 (WO) .................. PCT/FR2007/000269

(51) Int. Cl.
*A61K 49/00* (2006.01)
*B01F 17/00* (2006.01)
*A61K 9/107* (2006.01)

(52) U.S. Cl.
CPC ............ *A61K 49/0078* (2013.01); *A61K 9/1075* (2013.01); *A61K 49/0032* (2013.01); *A61K 49/0056* (2013.01); *B01F 17/0078* (2013.01)

(58) Field of Classification Search
None
See application file for complete search history.

(56) References Cited

U.S. PATENT DOCUMENTS

| | | | |
|---|---|---|---|
| 5,403,575 A * | 4/1995 | Kaufman et al. | 424/1.89 |
| 5,976,502 A * | 11/1999 | Khoobehi et al. | 424/9.6 |
| 6,350,431 B1 | 2/2002 | Snow et al. | |
| 6,559,183 B1 | 5/2003 | Schmid et al. | |
| 2004/0092428 A1 * | 5/2004 | Chen et al. | 514/2 |
| 2005/0079131 A1 | 4/2005 | Lanza et al. | |
| 2006/0222716 A1 * | 10/2006 | Schwarz et al. | 424/489 |

FOREIGN PATENT DOCUMENTS

| | | |
|---|---|---|
| WO | 98 48845 | 11/1998 |
| WO | 2008 102065 | 8/2008 |

OTHER PUBLICATIONS

Entry for "lecithin". Stedman's Medical Dictionary, 28th Edition. 2005 Lippincott Williams & Wilkins.*
Suppocire.TM. Standard product information. 2010 Gattefosse website <http://www.gattefosse.com/en/applications/?administration-route,rectal-vaginal,standard>. Accessed Aug. 9, 2012.*
Friedlander M, Theesfeld CL, Sugita M, Fruttiger M, Thomas MA, Chang S, Cheresh DA. Involvement of integrins alpha v beta 3 and alpha v beta 5 in ocular neovascular diseases. 1996 Proc. Natl. Acad. Sci. USA 93: 9764-9769.*
Lundberg. Preparation of drug-carrier emulsions stabilized with phosphatidylcholine-surfactant mixtures. 1994 J. Pharm. Sci. 83: 72-75.*
Kalchenko, V. et al., "Use of Lipophilic Near-Infrared Dye in Whole-Body Optical Imaging of Hematopoietic Cell Homing", Journal of Biomedical Optics, vol. 11, No. 5, pp. 050507-1-050507-3 (Sep. 2006) XP-002511213.
Primo, F. L. et al., "Binding and Photophysical Studies of Biocompatible Magnetic Fluid in Biological Medium and Development of Magnetic Nanoemulsion: A New Candidate for Cancer Treatment", Journal of Magnetism and Magnetic Materials, vol. 310, No. 2, pp. 2838-2840 (Mar. 2007) XP-002447726.
Weyenberg et al.—"Cytotoxicity of submicron emulsions and solid lipid nanoparticles for dermal application" International Journal of Pharmaceutics 337 (2007) pp. 291-298.

* cited by examiner

*Primary Examiner* — Michael G Hartley
*Assistant Examiner* — Jennifer Lamberski
(74) *Attorney, Agent, or Firm* — Oblon, McClelland, Maier & Neustadt, L.L.P.

(57) ABSTRACT

The invention relates to a fluorescent emulsion, to a diagnostic reagent containing the same, and to the use thereof in the preparation of a diagnostic reagent for in vivo fluorescence imaging.

24 Claims, 6 Drawing Sheets

PRIOR ART

FLUORESCENT EMULSIONS FOR OPTICAL IMAGING

The present invention relates to fluorescent probes which are in the form of nanoemulsions that can be used in the field of noninvasive in vivo functional imaging.

In vivo, the recent development of optical methods opens up new horizons for functional imaging. It is now possible to follow, in real time and noninvasively, what happens to luminescent molecules, their biodistribution, to establish a diagnosis and to evaluate the effect of a therapy by virtue of these molecules. Optical imaging has a certain number of advantages compared with the other functional imaging techniques such as magnetic resonance imaging (MRI), positron emission tomography (PET) imaging and single-photon emission computed tomography (SPECT) imaging:

- it avoids the handling of radioactive molecules, thus setting aside the constraints and the risks associated therewith (radioprotection, handling of waste, synchrotron source for PET labels);
- it does not require a large amount of money to be spent on equipment;
- it has good sensitivity compared with MRI, in terms of amount of label injected.

The applications envisioned in the short term for these optical functional imaging techniques are, in small animals, an aid to the discovery of biomarkers for targeting tumors or atheroma plaque, the discovery and evaluation of new therapeutic agents, and a decrease in the number of animals sacrificed in toxicity studies since these techniques enable longitudinal monitoring. In the very short term, applications in humans are envisioned in intra-operative surgery with the aim of allowing better delimiting of the borders of tumor exeresis for example. Other, medium-term applications are explored in dermatology, as a tool for diagnosing breast cancer or, by endoscopy, prostate cancer or precancerous colon polyps.

Fluorescence imaging requires the prior injection of an optical probe, which is the equivalent of the tracer in nuclear medicine or of the contrast agent in MRI or X-ray tomography. This optical probe is in general a molecular assembly constituted at least of a fluorescent label which corresponds to the entity responsible for the absorption and the emission of the fluorescence. This label may, for example, be an organic fluorophore, a lanthanide complex, or else a luminescent semiconductive nanocrystal ("quantum dot", such as CdSe, CdTe, InP, Si, etc.).

These optical probes may also comprise one or more of the following components:
a) a biological ligand, which makes it possible to image a specific biological process. Such a ligand may be:
i) a biological targeting ligand: it is then a biological entity (antibody, peptide, saccharide, etc.) or a chemical entity (folic acid, for example) which enables specific recognition of certain cells (for example, of tumor cells, as described for example in the article by S. Achilefu, Technology in Cancer Research & Treatment, 2004, 3, 393-408) or of certain organs,
ii) a biological ligand which is a marker for a given biological activity, for example, an enzymatic activity. For example, these biological ligands will be a peptide that can be cleaved by a given protease, at the end of which an inhibitor of the fluorescence of the label will be grafted. Ligands of this type make it possible to specifically image the enzymatic activity of the protease, as is reported in the article by C. H. Tung, Biopolymers, 2004, 76, 391-403. Another example consists of a biological ligand comprising a disulfide bridge separating the label from an inhibitor of the fluorescence of said label. This biological ligand then makes it possible to specifically image the internalization of the optical probe in a cell, as described, for example, in the French patent application published under the number FR 2 888 938;
b) a stealth agent: this is an entity which is added to the optical probe in order to confer on it stealth with respect to the immune system, to increase its circulation time in the organism, and to slow down its elimination;
c) an "assembly vector": this is an entity which can make it possible to assemble the fluorescent label(s) and/or the biological targeting ligand(s) and/or the stealth agent(s) and/or one or other functionalities (delivery of medicaments, other imaging mode, therapeutic function, for example).

On the basis of this general principle, four major types of probes have been described in the literature for noninvasive fluorescence imaging in small animals.

The first major type of optical probe corresponds to optical probes having, as label, one (or more) organic fluorophore(s) grafted directly on to the biological ligand. While the first organic fluorophore used in fluorescence imaging, ICG (Indo Cyanin Green), was used very early on "naked" (injection of the fluorophore alone) for imaging vascularization and circulation in blood vessels, these organic fluorophores have subsequently been grafted on to proteins or antibodies for targeting various cells. However, the coupling to these large molecules can have drawbacks in terms of targeting and pharmacokinetics, and for this reason, more recently, the functionalization of fluorophores with small peptides has been preferred. In general, optical probes of this first type have the following drawbacks:

- a biological ligand is labeled only with a small number of fluorescent labels (typically one fluorophore for a peptide, 3 to 4 for an antibody). To increase the number of fluorophores, it is otherwise necessary to use complex vector molecular structures (see hereinafter). They are therefore optical probes which result in weak fluorescence signals;
- the organic fluorophores used, the absorption and emission wavelengths of which should be in the near-infrared range (between 650 and 900 nm), an optical window for which light absorption and scattering in biological tissues are minimal, are generally sensitive to photobleaching, and in particular in an aqueous buffer (loss of fluorescence over time). The availability of organic fluorophores that can be grafted to bio-molecules and are soluble in an aqueous buffer, in this wavelength range is, moreover, limited. (Examples: cyanins sold by Amersham, the series of products sold under the trade name ALEXA® by Invitrogen), and they are very expensive, whereas many other inexpensive fluorophores for near-infrared are available from other suppliers, but unfortunately cannot be used for this application since they are not soluble in an aqueous medium; the optical probes should be able to be injected intravenously in large amounts since only a small portion of them reaches their target. In fact, the target-ligand recognition kinetics are often slow and compete with the processes of elimination by the organism. The addition of a stealth agent can make it possible to improve this point. Nevertheless, and this is the fourth drawback of these optical probes;
- the addition of a stealth agent (like, optionally, increasing the number of fluorescent labels per biological ligand, or adding other functionalities such as multimodality or the delivery of medicaments) requires the use of an "assembly vector" for assembling the various elements of the optical probe. The synthesis of these optical probes then becomes much more complex.

The second major type of optical probe corresponds to optical probes having, as label, a luminescent semi-conductive nanocrystal ("quantum dot" such as CdSe, CdTe, InP, Si, etc.), functionalized with a biological ligand.

The exceptional optical properties (absorption, emission, quantum yield of fluorescence) of these nanoparticles have over the past few years made them preferred labels for noninvasive imaging in small animals (X. Michalet et al., Science, 2005, 307, 538-544). However, while no toxicity has been observed during these experiments, the presence of heavy metals in the core of these nanocrystals remains a considerable damper when clinical applications in humans are envisioned (R. Hardman, Environmental Health Perspectives, 2006, 114, 165-172). Another thing currently blocking the use of these probes for noninvasive imaging is the control of their properties of interaction with biological tissues. In fact, these properties are highly dependent on the surface condition of these nanoparticles (presence of polyethylene glycol (PEG) chains) and on their size.

The third major type of optical probe corresponds to optical probes having, as label, inorganic nanoparticles of oxides, such as, for example, nanoparticles of silica, encapsulating and/or on to which are grafted organic fluorophores or lanthanide chelates. Up until now, few studies have used this type of optical probe in vivo, other than the studies by the team of P. Prasad in nanomedicine (I. Roy et al., PNAS, 2005, 102(2), 279-284), although the synthesis of labels of this type is thoroughly described in the literature. Like the semiconductive nanocrystals described above, these inorganic nanoparticles require a very advanced surface chemistry in order to graft stealth agents thereto, which make them compatible with living organisms.

Finally, the fourth major type of optical probe corresponds to optical probes having, as label, organic nanoparticles encapsulating and/or on to which are grafted organic fluorophores or lanthanide chelates. Among said nanoparticles are listed:

polymer nanospheres encapsulating organic fluorophores, as described, for example, in the article by V. Holzapfel et al., J. Phys.: Condens. Mater., 2006, 18, 52581-S2594;

polymersomes which are assemblies of amphiphilic synthetic polymers in the form of nanospheres made up of a double layer of polymers in a manner similar to liposomes, which, for their part, are made up of lipids. These polymersomes can be used to encapsulate organic fluorophores as described, for example, in American patent application No. US 2005/0019265 or in the article by P. Ghoroghchian et al., Proc. Natl. Acad. Sci. USA, 2004, 102(8), 2922-2927.

Although these nanoparticulate systems are organic, they have a certain number of drawbacks. The polymersomes and the liposomes show problems of chemical and physical stability. As regards the polymer nanospheres, their cytotoxicity and their chemical synthesis (problem of residual solvent) limit their use. Even the synthetic polymers, which show good biodegradability and low cytotoxicity in vitro such as lactic acid polymers (PLA), poly($\beta$-hydroxybutyrate) (PHB) polymers or alternatively poly(lactide-co-glycolide), have cytotoxic effects when they are delivered in the form of nanoparticles.

The optical probes used for fluorescence imaging that have been described up until now in the literature therefore generally have one or more of the following drawbacks:

a weak fluorescence per biological ligand, especially in a biological medium, a tendency toward photobleaching, a complex surface functionalization or assembly chemistry, potential toxicity when they are in the form of inorganic nanoparticles, which would require the use of additional surface chemistry in order to make them biocompatible, thus making them difficult to use in human imaging;

complex synthesis, insofar as inorganic nanoparticles are difficult to synthesize, in particular in large amounts, and require the use of toxic solvents such as trioctylphosphine (TOP) and trioctylphosphine oxide (TOPO), and of dangerous materials ($Cd(Me)_2$, etc.). The cost prices of these syntheses are, moreover, very high;

weak stability and relatively nonreproducible synthesis of organic nanoparticles (polymersomes); cytotoxicity of organic nanoparticles of polymer and large-scale synthesis not yet mastered;

fluorescence lifetime too short, preventing their use for time-resolved fluorescence imaging.

The use of time-resolved fluorescence techniques has many advantages compared with stationary methods.

Firstly, it is the favorite technique when working in the fluorescent mode since the signal measured potentially contains all the information on the structure of the medium and on the fluorophores. In fact, techniques using continuous-wave (CW) signals are based on the simple measurement of the reduction in the incident signal. The distribution of fluorescent molecules is determined by measuring the fluorescence signal, which is directly proportional to the local concentration of fluorescent molecules. This technique therefore assumes knowledge of the optical properties (of absorption and of scattering) of the surrounding scattering medium, and does not take into account the intrinsic properties of the fluorophore related to the lifetime. The use of time-resolved signals (signals modulated in terms of amplitude over time or pulsed signals) offers the possibility both of lifting the uncertainty regarding the optical properties (of scattering and of absorption) of the medium—which makes it possible to obtain better modeling of the physical phenomenon of light propagation—and of using the information regarding the lifetime of the fluorophore to identify its position with greater accuracy.

Secondly, for in vivo detection on cells, biological tissues or even an animal or in humans, the use of pulsed techniques also makes it possible to reduce the overall dose of irradiation applied, while at the same time having sufficient peak power levels for very sensitive detection. However, in a medium which is highly scattering or autofluorescent, as biological tissues are, the sensitivity of detection of the specific signal of the fluorescent probes can be reduced by the autofluorescence or the nonspecific scattering of the medium. The problem is that the medium, even if its intrinsic autofluorescence properties are weak, is present in predominant amount compared with the fluorophore to be detected. Whatever the experimental configuration used (fluorescence reflectance imaging: FRI or transillumination fluorescence imaging: TFI), it must be possible to optically filter out the fluorescence of the fluorophore from the autofluorescence and from the scattering of the excitation signal, but also to differentiate, on the signal collected at the detector, the fluorescence of the fluorophore from the autofluorescence and from the scattering of the excitation signal.

The autofluorescence lifetime of the medium is generally very short (of the order of 200 to 500 ps typically). In order to differentiate as much as possible between the fluorescent probes and this autofluorescent background and to benefit completely from time-resolved methods compared with stationary methods, it is therefore favorable to use highly luminous fluorescent probes which have a "long" fluorescence lifetime, greater than 0.5 ns. On the other hand, the use of fluorophores where the lifetime is too long does not make it possible to correctly record a decline in the signal between two acquisitions. There is then no additional information compared with the information obtained with a measurement using a continuous excitation. In addition, also this does not enable the signal to return to zero between two acquisitions. The pulsed optical acquisition systems used in the clinical field typically operate at 8 MHz. It is not possible to work above approximately 10 MHz, otherwise the tissues are burnt. If one works at frequencies that are too low, signal sensitivity is, however, lost. It is necessary, therefore, in order to take advantage of time-resolved methods, to use fluorophores with a fluorescence lifetime of less than 10-20 ns, in order for the signal to have returned to close to zero over the course of an acquisition window of 100-125 ns (frequency of 8-10 MHz).

The ideal fluorescence lifetime range for time-resolved fluorescence imaging is, consequently, between 0.5 ns and 10 ns. Now, for applications in a biological medium or in a turbid medium, working in the near-infrared range (640-900 nm), for which the scattering and also the absorption of light by the tissues or the autofluorescence of the tissues are reduced compared with the visible range, is absolutely essential. At the current time, there is virtually no suitable fluorophore which absorbs and emits in the near-infrared range (640-900 nm) with fluorescence lifetimes of between 0.5 and 10 ns.

Nanoemulsions, sometimes called miniemulsions, ultrafine emulsions or alternatively submicronic emulsions, are emulsions of which the diameter is generally between 10 and 200 nm. In summary, an emulsion is a mixture of two immiscible liquid substances, made up of a continuous phase and a dispersed phase. One substance is dispersed in the second substance (continuous phase) in the form of small droplets (dispersed phase). The mixture remains stable by virtue of the action of amphiphilic molecules, called emulsifiers or surfactants, which become placed at the interface between the two phases. Emulsions are metastable supramolecular structures. These structures are to be distinguished from polymersomes and micelles.

Polymersomes (family comprising liposomes) are vesicles of a few tens to a few thousand nm in diameter. These vesicles are composed of one or more bilayers of surfactants which make(s) it possible to separate the intravesicular medium from the external medium, the two media being of the same nature (aqueous).

Micelles consist of self-assembled surfactant aggregates, a few nanometers in diameter. The surfactants are organized in such a way as to orient their hydrophilic part toward the outside (the solvent) and their hydrophobic chains toward the core of the micelle.

Emulsion systems intended for various applications in the medical field have already been described in the literature:
  parenteral nutrition systems, which are emulsions based on lipids injected intravenously as a source of essential fatty acids, of lipophilic vitamins and of energy. These emulsions are generally made up of a mixture of oils of natural origin (plant oil or fish oil);
  drug delivery systems, which are emulsions of oil-in-water type studied and used in particular for the encapsulation of relatively water-insoluble active ingredients. These emulsions have the advantage of improving the bioavailability of the active ingredient that they contain and of reducing the side effects thereof, but also of increasing the stability thereof by limiting the hydrolysis thereof. Emulsions are used for three different methods of administration: ocular/parenteral/oral. In order to limit the metabolization of the emulsions administered parenterally, certain formulations make use of stealth cosurfactants, thus increasing the circulation time of the emulsions in the blood system;
  systems containing dyes that can be used as histological markers for the resection of cancerous tumors. Such emulsions are, for example, described in international application WO 98/48845, which illustrates in particular an oil-in-water emulsion in which the oil droplets are constituted of sesame oil containing a particular chromophore, Sudan III, which absorbs at a wavelength of 507 nm;
  imaging systems using emulsion-based contrast agents. These systems were developed for magnetic resonance imaging (MRI), as is, for example, described in the article by P. M. Winter, et al., Cancer Research, 2003, 63, 5838-5843 and for X-ray imaging, as described, for example, in patent application US 2005/0079131.

The contrast agent for MRI designed by Winter et al. (mentioned above) is an emulsion of a fluorocarbon oil (for example, perfluorooctyl bromide), in water stabilized with a layer of surfactants. The mixture of surfactants used is in particular composed of gadolinium chelates, such as gadolinium-diethylenetriaminepentaacetic acid-bis-oleate (Gd-DTPA-BOA) at a content of 30% (mol). These compounds are chelating agents which act as MRI label by virtue of their magnetic properties. The targeting of tumors is provided by the addition of a small amount of distearoylphosphatidylethanolamine poly(ethylene glycol 2000)-maleimide (DSPE-PEG (2000)-maleimide) coupled to a peptidomimetic antagonist of $a_v\beta_3$ integrins, in the layer of surfactants (0.5% mol). The nanoparticles will then target the cells expressing $a_v\beta_3$ integrins, which are proteins associated with the angiogenesis that accompanies tumor growth.

The contrast-agent properties in these nanoparticles are therefore conferred by the surfactants. Furthermore, the diameter of these particles, approximately 270 nm, is relatively large and the polydispersity is high. The authors Winter et al. estimate, moreover, that the diffusion of the nanoparticles to the tumors is limited by their large size. These nanoparticles make it possible, however, to increase the MRI signal by 126% in the targeted zones.

The nanoparticles described in patent application US 2005/0079131 are also oil-in-water emulsions, which are formed by a lipophilic compound coupled to an element having a high atomic number (Z) such that Z>36, which are stabilized by a layer of surfactants based on lecithin and on cholesterol. In this formulation, prepared by a microfluidizer, it is the oil which acts as X-ray contrast agent by virtue of its heavy atom Z>36. The targeting is again provided here by the use of DSPE-PEG (2000)-maleimide coupled to a peptidomimetic antagonist of $a_v\beta_3$ integrins. The nominal size of the particles is less than 200 nm. However, this patent application does not mention any in vivo biological test in live animals with this type of emulsion. Moreover, no stealth agent is surface-grafted so as to allow homogeneous biodistribution of the contrast agent in the body. It is, moreover, indicated in this patent application that the nanoparticle may also include a fluorophore, at its surface (within the layer of surfactants), it being possible for said fluorophore in particular to be fluorescein, as ancillary imaging agent. It should be noted, however, that fluorescein is not a fluorophore which absorbs/emits in the near-infrared range, and it cannot therefore be used for noninvasive in vivo imaging in small animals. In addition the presence of an element with a high atomic number in the oil has the drawback of inhibiting the fluorescence of the nanoparticles.

Therefore, in order to remedy all the problems encountered during the production or the use of the existing systems, the inventors have developed what forms the subject of the invention.

The inventors, in fact, gave themselves the objective of providing a fluorescent probe which does not have the drawbacks of the fluorescent probes currently available and which is simple to prepare and to use, in particular in noninvasive in vivo imaging in small animals. The inventors more particularly gave themselves the objective of providing a formulation which makes it possible, on the one hand, to optionally increase the quantum yield of fluorescence of fluorophore compounds which emit and absorb in the near-infrared range and, on the other hand, to increase the fluorescence lifetime to a value greater than 0.5 ns, so as to be able to use time-resolved fluorescence imaging techniques in a scattering medium (in vivo pulsed imaging).

A subject of the present invention is therefore a fluorescent emulsion of oil-in-water type, comprising at least one aqueous continuous phase and at least one oily dispersed phase, said emulsion being characterized in that the dispersed phase is made up of droplets of at least one biocompatible oil having an average diameter of greater than or equal to 10 nm and less than or equal to 200 nm, and in that said droplets of oil contain at least one lipophilic fluorophore which absorbs and emits at a wavelength of between 640 and 900 nm, said droplets being stabilized by a surfactant layer located at the periphery of said droplets, said layer comprising, as a mixture, at least one amphiphilic surfactant and at least one stealth cosurfactant.

This emulsion has the following advantages:
- it is composed of biocompatible organic materials, a large part of which can be assimilated by the organism into which it may be injected;
- it is particularly stable over time, especially in terms of particle size and of fluorescence properties;
- it constitutes a molecular probe for fluorescence imaging in small animals (in vivo) in which the fluorescent organic molecules are encapsulated and therefore undetectable by the organism;
- this molecular probe is designed so as to have a long circulation time in the organism. This leads to an increase in the chances of target-ligand recognition;
- owing to their presence directly at the heart of the oil droplets, i.e. inside the oil droplets and not at their periphery, a large number of fluorescent molecules are associated with the recognition of a target by a ligand, which allows better sensitivity of detection.

For the purpose of the present invention, the term "droplet" encompasses both the droplets of liquid oil per se, and also the solid particles derived from emulsions of oil-in-water type, in which the oil used is a crystallizable oil. In the latter case, the term "solid emulsion" is then used.

The fact that the lipophilic fluorophore is incorporated directly into the oil droplets provides the following further advantages:
- of protecting the fluorophore from the aqueous environment, in which the photobleaching (loss of fluorescence in the presence of light) thereof is more rapid;
- of encapsulating a large number of fluorophores while at the same time leaving free the surface grafting functions of the nanoparticles for the functionalization thereof with biological ligands. Thus, no bond for surface grafting of the nano-particle needs to be sacrificed for the grafting of fluorophores; they can all be used for the grafting of targeting ligands, the surface density of which can thus be higher;
- through the choice of the fluorophores present in the heart of the oil droplets of the emulsion in accordance with the invention; the fluorophores used in the invention are lipophilic fluorophores which absorb/emit in the near-infrared range;
- through the presence of stealth agents so as to give the nanoparticle the appropriate pharmacodynamics: these stealth agents make it possible both to increase the stability of the emulsions and also to "deceive" the immune defenses of the organism;
- through the increase in the fluorescence lifetime and, for some, in the quantum yield of the fluorophore compounds present at the heart of the oil droplets; this makes it possible to have access to time-resolved fluorescence (pulsed fluorescence) imaging in a scattering medium. Thus it becomes, in particular, possible to obtain quantum yields in water and in aqueous buffers that are unequalled for this wavelength range: of 24% for 1,1'-dioctadecyl-3,3,3',3'-tetramethyl-indotricarbocyanin iodide (DiR) and of 37% for 1,1'-dioctadecyl-3,3,3',3'-tetramethylindodicarbocyanin perchlorate (DiD) when they are formulated in a nanoemulsion in accordance with the present invention, whereas, to our knowledge, the quantum yields of fluorescence of the organic fluorophores which absorb and emit between 640 and 900 nm, including commercial organic fluorophores such as, for example, Alexa 750 (sold by the company Invitrogen), Cy7 and Cy7.5 (sold by the company GE-Healthcare), or IR dye 800 (sold by the company Li-Cor), are a maximum of 10-15% when these fluorophores are formulated in water or in an aqueous buffer.

The size of the oil droplets in the emulsion is preferably between 10 and 80 nm, limits included. The inventors have observed in fact that the cell internalization threshold lies approximately around 80 nm. For larger sizes, no internalization is observed.

According to the invention, the biocompatible oils are chosen from natural oils of plant or animal origin, synthetic oils and mixtures thereof. These oils are used without chemical or physical modification prior to the formation of the emulsion.

Among such oils mention may in particular be made of oils of plant origin, among which are in particular soybean oil, palm oil, groundnut oil, olive oil, flax oil, grapeseed oil and sunflower oil; oils of animal origin, among which are in particular fish oils; synthetic oils, among which are in particular triglycerides, diglycerides and monoglycerides; it being possible for said oils to be used alone or as mixtures.

These oils may be first-expression, refined or interesterified oils.

According to one particularly preferred embodiment of the invention, these oils are chosen from oils which are not very water-soluble, i.e which have a hydrophilic-lipophilic balance (HLB) generally of less than 8, and even more preferably of between 3 and 6, such as, for example, soybean oil, or alternatively from crystallizable oils (waxes) rich in $C_8$-$C_{18}$, principally $C_{12}$-$C_{14}$, saturated fatty acid glycerides, such as the mixtures of semi-synthetic glycerides sold under the trade name of SUPPOCIRE® N by the company Gattefosse. Among such mixtures, the product sold under the name SUPPOCIRE® NC by Gattefosse is particularly preferred. This product is solid at ambient temperature and is obtained by direct esterification of fatty acids and of glycerol. It has the following quali-quantitative composition:

$C_8$: 0.1 to 0.9%
$C_{10}$: 0.1 to 0.9%
$C_{12}$: 25 to 50%
$C_{14}$: 10 to 24.9%
$C_{16}$: 10 to 24.9%
$C_{18}$: 10 to 24.9%.

According to one particular and preferred embodiment of the invention, the oily phase is composed of at least one plant or animal oil and of at least one crystallizable oil rich in $C_8$-$C_{18}$ saturated fatty acid glycerides.

The use of such a mixture makes it possible to improve the solubilization of the fluorophore(s) within the oily phase and thus to improve the optical properties of the fluorophores encapsulated.

In this case, the ratio by weight of plant or animal oil/crystallizable oil rich in glycerides preferably ranges between 10/90 and 90/10, limits included, and even more preferably between 20/80 and 80/20, limits included.

According to one preferred embodiment, the oily phase is made up of at least 10% by weight of an oil of which the viscosity is greater than or equal to 100 cP at 20° C. (viscosity values tabulated, for example, in the *Handbook of Chemistry and Physics*, CRC Press, 88th edition, 2007). The presence of such an oil in the oily phase makes it possible to confer, on the fluorophores formulated in the nanoemulsions, fluorescence lifetimes particularly suitable for in vivo time-resolved fluorescence imaging.

According to the invention, the nature of the amphiphilic surfactant(s) providing the stabilization of the oil droplets within the emulsion is not critical. These amphiphilic surfactants (comprising a hydrophilic part and a lipophilic part) are generally chosen from compounds of which the lipophilic part comprises a linear or branched, saturated or unsaturated chain containing from 8 to 30 carbon atoms. They may be chosen from phospholipids, cholesterols, lysolipids, sphingomyelins, tocopherols, glucolipids, stearylamines, cardiolipins of natural or synthetic origin; molecules composed of a fatty acid coupled to a hydrophilic group by an ether or ester function, such as sorbitan esters, for instance the sorbitan monooleate and monolaurate sold under the name SPAN® by the company Sigma; polymerized lipids; lipids conjugated to short chains of polyethylene oxide (PEG) such as the nonionic surfactants sold under the trade names TWEEN®. by the company ICI Americas Inc. and TRITON®. by the company Union Carbide Corp.; sugar esters, such as sucrose monolaurate and dilaurate, sucrose monopalmitate and dipalmitate, and sucrose monostearate and distearate; it being possible for said surfactants to be used alone or as mixtures.

According to the invention, the surfactant(s) is (are) preferably surfactants that are of natural origin and are assimilable (biocompatible), such as soybean lecithin, phospholipids and cholesterol.

The nature of the lipophilic fluorophore(s) that can be used in the emulsion in accordance with the invention is not essential provided that they are compatible with in vivo fluorescence imaging and that they absorb and emit at a wavelength of between 640 and 900 nm. This is because, in order for the excitation light and the light emitted by the fluorophore to be able to pass through the tissues, it is advisable to use fluorophores which absorb and emit in the near-infrared range. By way of a lipophilic fluorophore, mention may, for example, be made of the compounds described in chapter 13 ("Probes for Lipids and Membranes") of the Invitrogen catalog.

More specifically, in particular mention may be made, by way of fluorophore, of fatty acid analogs; sphingolipids, steroids, lipopolysaccharides and phospholipids functionalized with a group which absorbs and emits in the near-infrared range (640-900 nm), and amphiphilic derivatives thereof. Among such fluorophores, mention may more particularly be made of the derivatives of cyanins, of rhodamines, of fluoresceins, of coumarins, of squaraines, of azulenes, of xanthenes, of oxazines and of 4,4-difluoro-4-bora-3a,4a-diaza-s-indacene (boron dipyrromethene), and also amphiphilic derivatives of said fluorophores.

By way of example, mention may be made more particularly of the fluorescent products sold under the trade names BODIPY® 665/676 (Ex/Em.) by the company Invitrogen; amphiphilic derivatives of dialkylcarbocyanins, such as the 1,1'-dioctadecyl-3,3,3',3'-tetramethylindodicarbocyanin perchlorate (DiD) sold under the reference D-307 by the company Invitrogen and the 1,1'-dioctadecyl-3,3,3',3'-tetramethylindotricarbocyanin iodide (DiR) sold under the reference D-12731 by the company Invitrogen.

According to one preferred embodiment of the invention, the fluorophores are chosen from amphiphilic derivatives of dialkylcarbocyanins.

The stealth cosurfactant(s) that can be used in the emulsions in accordance with the present invention are preferably amphiphilic molecules of which the hydrophilic part is completely or partially composed of a polyethylene oxide chain (PEO or PEG) and in which the number of PEO units preferably ranges between 2 and 500. The stealth cosurfactants may also be polysaccharide compounds, such as dextrans, for example. By way of example of stealth cosurfactants that can be used according to the present invention, mention in particular may be made of polyethylene glycol/phosphatidylethanolamine (PEG/PE) conjugate compounds, fatty acid ethers of polyethylene glycol, such as the products sold under the trade name BRIJ® (for example, BRIJ®. 35, 58, 78 or 98) by the company ICI Americas Inc., fatty acid esters of polyethylene glycol, such as the products sold under the trade name MYRJ® by the company ICI Americas Inc. (for example, MRYJ® 45, 52, 53 or 59), and ethylene oxide/propylene oxide block copolymers, such as the products sold under the trade name PLURONIC® by the company BASF AG (for example, PLURONIC® F68, F127, L64 or L61) or the products sold under the trade name SYNPERONIC®. by the company Unichema Chemie BV (for example SYNPERONIC® PE/F68, PE/L61 or PE/L64).

According to one preferred embodiment of the invention, the surfactant layer located at the periphery of the oil droplets of the emulsion also comprises at least one agent for targeting a biological activity of interest, said targeting agent being made up of an amphiphilic grafting cosurfactant of which the hydrophilic part is covalently bonded to a biological ligand. The presence of a targeting agent makes it possible to target a biological process of particular interest.

According to one advantageous form of the invention, said targeting agents are chosen from the compounds of formula (I) below:

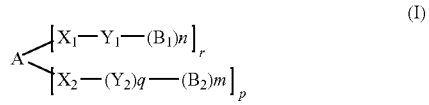

(I)

in which:

A is the lipophilic part of an amphiphilic grafting cosurfactant (CoTA), $X_1$ and $X_2$, which may be identical or different, constitute the hydrophilic part of said cosurfactant CoTA and are composed of a flexible spacer arm chosen from saturated or unsaturated, linear or branched carbon-based chains optionally substituted, interrupted and/or terminated with one or more heteroatoms chosen, for example, from N, O, P and S, and/or with one or more groups chosen, for example, from $C_1$-$C_4$ alkyl or $C_1$-$C_4$ alkoxy radicals, or with one or more functions chosen from ether, ester, amide, carbonyl, carbamate, urea, thiourea and disulfide functions;

$Y_1$ and $Y_2$, which may be identical or different, are chosen from chemical groups capable of linking $X_1$ and $B_1$, respectively $X_2$ and $B_2$, by covalent bonds;

$B_1$ and $B_2$, which may be identical or different, are biological ligands, one of the ends of which is involved in the covalent bond formed with $X_1$, respectively $X_2$;

n is an integer between 1 and 20, limits included;

q is an integer equal to 0 or 1;

m is an integer between 0 and 20, limits included, it being understood that m=0 when q=0;

p is an integer between 0 and 10, limits included; and

R is an integer between 0 and 10, limits included.

The lipophilic part (A) of the grafting cosurfactant CoTA present in the targeting agent of formula (I) enables it to anchor itself to the surface of the oil droplets within the peripheral surfactant layer. It may be composed in particular of a saturated or unsaturated, linear or branched $C_6$-$C_{26}$ alkyl chain.

The hydrophilic part of the CoTA constituting the spacer arms $X_1$ and $X_2$ of the compounds of formula (I) above may in particular be chosen from chains made up of polyoxyethylene or dextran units.

According to one advantageous embodiment of the invention, the covalent bonds (functional groups $Y_1$/$Y_2$) providing the attachment of $X_1$/$X_2$ to the $B_1$/$B_2$ units are derived from the reaction between a chemical function initially carried by the hydrophilic part of the CoTA before its reaction with $B_1$/$B_2$, and a complementary chemical function carried by the biological ligands $B_1$/$B_2$ before the reaction thereof with $X_1$ respectively $X_2$. By way of nonlimiting and nonexhaustive example, mention may be made in particular of the covalent bonds resulting from the reaction:

of an amine and of an ester that is activated, for example with an N-succinimidyl group, resulting in the formation of amide bonds;

of an oxyamine and of an aldehyde, resulting in the formation of oxime bonds; and of an maleimide and of a thiol, resulting in the formation of thioether bonds.

Among the biological ligands that can be used as $B_1$/$B_2$ units of the targeting agents of formula (I) above, mention may be made in particular of:

i) biological ligands which make it possible to target specifically certain cells, such as peptides, for example, the RGD peptide (linear or cyclized), their derivatives and their analogs (for example: the octeotrate peptide, an analog of somatostatin, an analog of bombesin, neurotensin, EGF, VIP, etc.); proteins, antibodies, their derivatives or their analogs; monosaccharides such as glucose, oligosaccharides, polysaccharides, their derivatives and their analogs; oligonucleotides, DNA, their derivatives and their analogs; organic molecules such as folate, bisphosphonate pamidronate and organometallic complexes, the targeting activity of which is due to the molecular recognition of these ligands by receptors overexpressed at the surface of the cells of the region of interest;

ii) biological ligands which are markers for a given biological activity, for example, for an enzymatic activity. By way of example of such ligands, mention may, for example, be made of peptides that can be cleaved by a given protease, at the end of which an inhibitor of the fluorescence of the label will be grafted. Ligands of this type make it possible to specifically image the enzymatic activity of the protease (C. H. Tung, mentioned above). Another example consists of the biological ligands comprising a disulfide bridge separating the label from an inhibitor of its fluorescence. Such a biological ligand then makes it possible to specifically image the internalization of the optical probe in a cell, as described, for example, in patent application FR 2 888 938.

The coupling of the biological ligands to the grafting cosurfactants CoTA can be carried out either before emulsification or after emulsification. In the latter case, it is necessary for the chemical reactions employed to be compatible with the colloidal stability of the emulsions. They should be in particular carried out in an aqueous solution at a pH that is neither too acidic nor too basic (pH 5-11).

The continuous phase of the emulsion in accordance with the invention is an aqueous phase, preferably made up of water and/or of a physiologically acceptable buffer, such as a phosphate buffer, for example PBS (phosphate buffered saline) or of a sodium chloride solution.

The emulsion in accordance with the invention may be prepared by any conventional method known to those skilled in the art for preparing emulsions, for example according to a method comprising the following steps:

a) the preparation of an oily premix for the dispersed phase of the emulsion, consisting in mixing the various biocompatible oily constituents in an organic solvent such as, for example, chloroform so as to obtain, after evaporation of the solvent, a homogeneous oily premix for the dispersed phase, b) the preparation per se of the dispersed phase of the emulsion by homogeneous mixing of said oily premix with at least one lipophilic fluorophore which absorbs and emits in the near-infrared range;

c) the preparation of the continuous phase of the emulsion by mixing, in an aqueous phase, preferably under hot conditions, at least one amphiphilic surfactant, at least one stealth cosurfactant and optionally at least one agent for targeting a biological activity of interest, said targeting agent being made up of an amphiphilic grafting cosurfactant of which the hydrophilic part is covalently bonded to a biological ligand;

d) the addition of the continuous phase to the dispersed phase and the emulsification of the resulting mixture until a homogeneous emulsion is obtained in which the average diameter of the oil droplets is greater than 10 nm and less than 200 nm. This emulsification may, for example, be carried out using a sonicator, for a period of between 4 and 10 minutes.

According to one particular embodiment, and when the oily phase of the nanoemulsion is composed of at least one plant or animal oil or of at least one crystallizable oil rich in $C_8$-$C_{18}$ fatty acid glycerides, the surfactant used to stabilize the nanoemulsion can be incorporated completely or partially into the dispersed phase during step b) above. This embodiment makes it possible to prevent the formation of liposomes during the preparation of the nanoemulsion in accordance with the invention and is particularly advantageous when said surfactant is soybean lecithin.

Before its use, the emulsion is then preferably diluted, for example, 50/50, and sterilized, for example, by filtration. This filtration step makes it possible, moreover, to eliminate the possible aggregates which might have formed during the preparation of the emulsion.

As has been amply described and explained above, the fluorescent emulsions in accordance with the invention may be used for the detection of a biological activity of interest in vivo.

A second subject of the present invention is therefore the diagnostic reagent for diagnosing a biological activity of interest, characterized in that it comprises at least one fluorescent emulsion in accordance with the invention and as described above.

According to one particular and preferred embodiment of the invention, the reagent is an in vivo diagnostic reagent.

Finally, a subject of the invention is the use of at least one fluorescent emulsion as described above, for the preparation of a diagnostic reagent for diagnosing a biological activity of interest in vivo by fluorescence imaging and in particular by time-resolved fluorescence (pulsed fluorescence) imaging and/or for aiding in the development and optimization of therapeutic tools, such as medicaments. In fact, such a reagent can enable:
- the detection of cancerous cells in animals, optionally in humans, by fluorescence imaging, preferably by noninvasive fluorescence imaging;
- the detection of atheroma plaques in animals, optionally in humans, by fluorescence imaging, preferably by noninvasive fluorescence imaging;
- the detection of β-amyloid fibers characteristic of neurodegenerative diseases in animals, optionally in humans, by fluorescence imaging, preferably by noninvasive fluorescence imaging;
- the in vivo monitoring of enzymatic processes in animals, optionally in humans, by fluorescence imaging, preferably by noninvasive fluorescence imaging;
- the in vivo monitoring of gene expression in animals, by fluorescence imaging, preferably by noninvasive fluorescence imaging;
- the evaluation of a therapy in animals, by fluorescence imaging, preferably by noninvasive fluorescence imaging; or else
- the monitoring of the biodistribution of a drug, of the controlled delivery thereof, and of the effectiveness thereof.

In addition to the above arrangements, the invention also comprises other arrangements which will emerge from the description which follows, which refers to examples of preparation of fluorescent emulsions in accordance with the present invention, to a comparative example using such an emulsion for in vivo fluorescence imaging, and to examples demonstrating the effect of the formulation of fluorophore compounds in the form of a nanoemulsion on the fluorescence lifetime and the quantum yield of fluorescence, and also to the attached FIGS. 1 to 11.

It should be understood, however, that these examples are given purely by way of illustration of the invention, of which they in no way constitute any limitation.

EXAMPLE 1

Preparation of Nonfunctionalized Fluorescent Nanoemulsions

1) Preparation of a Premix for the Dispersed Phase

A premix made up of 15% w/w of soybean oil (Sigma-Aldrich), of 45% w/w of semisynthetic glycerides sold under the trade name SUPPOCIRE®NC (Gattefosse) and of 40% w/w of soybean lecithin (75% enriched in phosphatidylcholine) sold by the company Lipoid under The trade name LIPOID® S75 was prepared. These compounds were dissolved in chloroform, and the solution was subsequently evaporated under reduced pressure and dried at 50° C. so as to obtain a premix in the form of a viscous oil that solidifies upon cooling.

2) Preparation of the Dispersed Phase

A 0.833 g sample of the premix prepared above in the preceding stage was taken, at a temperature of approximately 70° C., and 1.5 mg of 1,1'-dioctadecyl-3,3,3',3'-tetramethylindodicarbocyanin (DiD) which is an oily fluorophore sold under the reference D-307 by the company Invitrogen, were added to said premix. The solution was homogenized by vortex, and maintained at 70° C. in anticipation of the emulsification phase.

3) Preparation of the Continuous Phase

The continuous phase was composed of 0.125 g of glycerol, 0.55 g of polyoxyethylene stearate comprising 50 mol of ethylene oxide, sold under the trade name MYRJ®53 by the company ICI Americas Inc., and a phosphate buffer solution (PBS) so as to make the weight up to 4.166 g. This solution was heated to 70° C. in anticipation of the emulsification.

4) Emulsification

The continuous phase was added to the dispersed phase and the mixture emulsified for 6 minutes for a total energy of 6000 joules with an AV505® sonicator equipped with a conical probe 3 mm in diameter (Sonics, Newtown).

5) Preparation for Intravenous Injection in Mice

The emulsion obtained above was then diluted by a factor of 6.25 with PBS, and then filtered through a 0.22 μm polyvinylidene fluoride (PVDF) filter sold under the trade name MILLEX®-GV by the company Millipore Corporation, so as to remove the aggregates, but also to sterilize it.

This emulsion can subsequently be directly used as a fluorescent probe for in vivo functional imaging.

Figure 1:
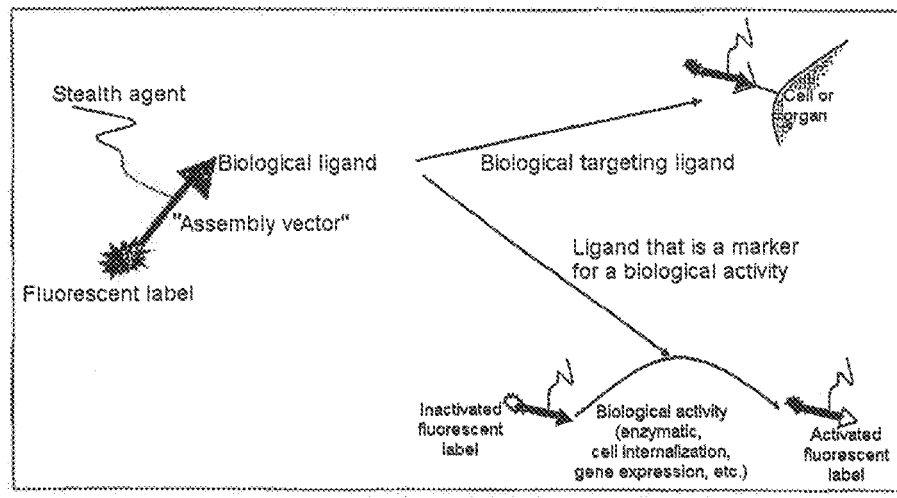
FIG. 1 is a diagrammatic representation of the various entities that may make up an optical probe for fluorescence imaging.
Figure 2:
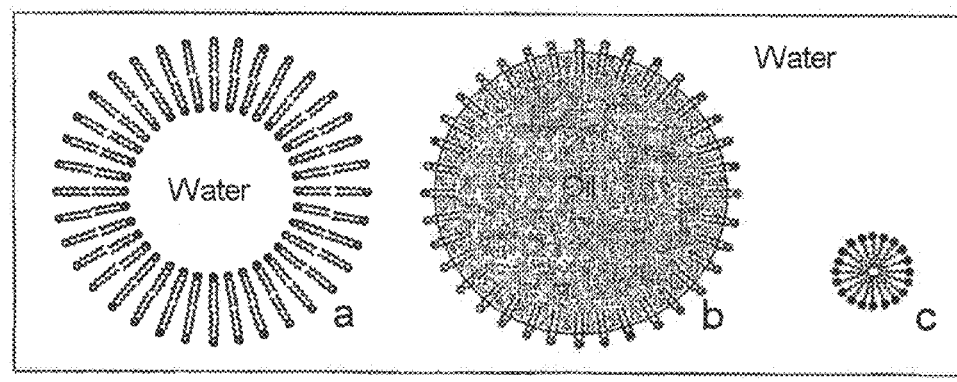
FIG. 2 is a comparative representation of the structure of a nanoemulsion (b) compared with micellar systems (c) and with polymersomes (a), the structures (a), (b) and (c) all having in common the fact that water is the continuous phase of the dispersion.
Figure 3:
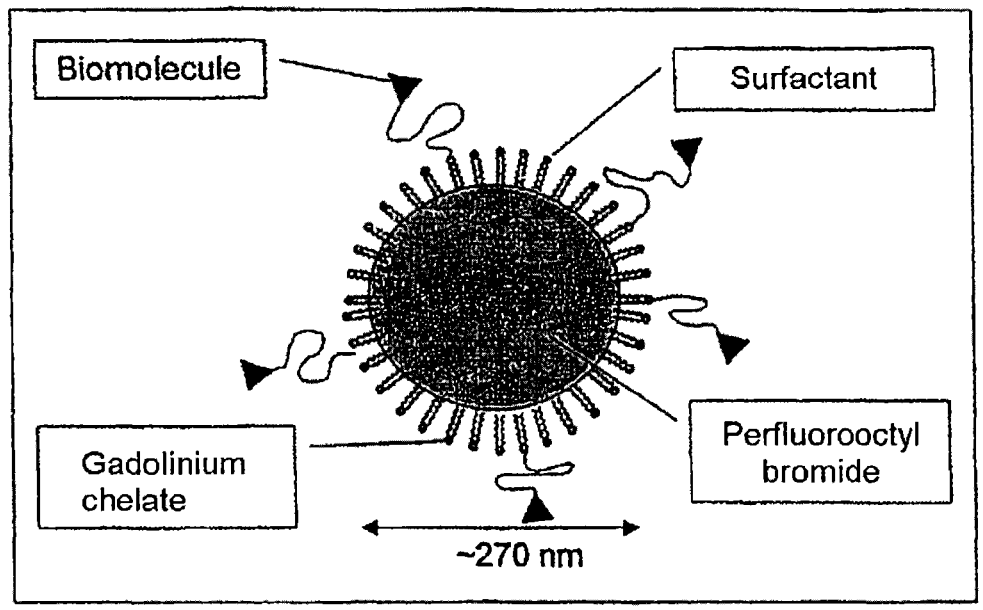
FIG. 3 corresponds to the diagram of the contrast agent described by Winter et al. (mentioned above), made up of an oil-in-water emulsion in which the aqueous continuous phase contains a dispersion of droplets (diameter approximately 270 nm) of perfluorooctyl bromide stabilized with surfactants, in particular composed of gadolinium chelates, attached to some of which is DSPE-PEG (2000)-maleimide coupled to a peptidomimetic antagonist of $a_v\beta_3$ integrins.
Figure 4:
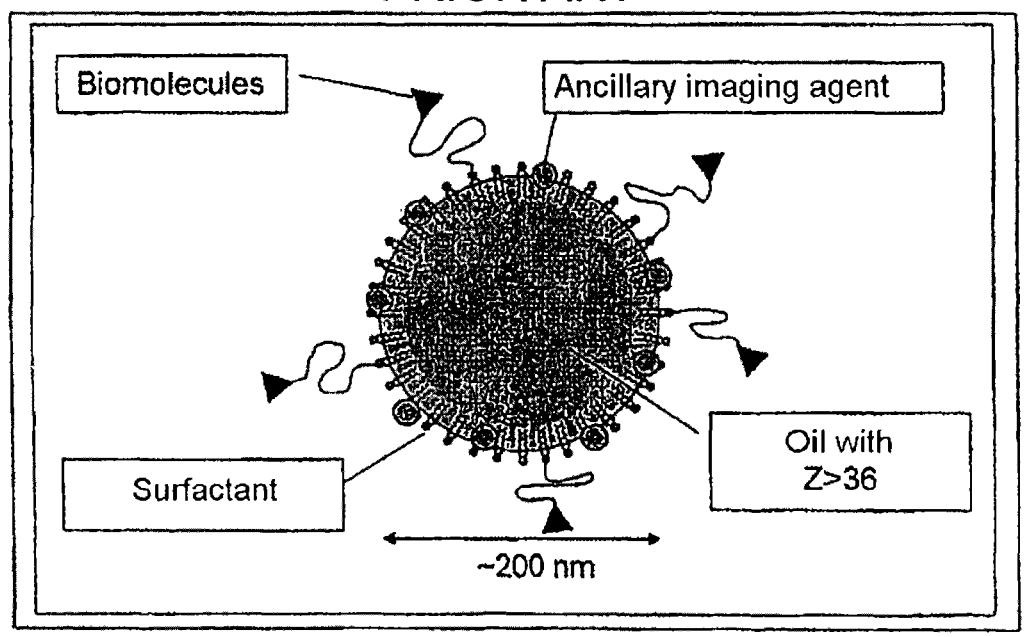
FIG. 4 corresponds to the diagram of the contrast agent described in patent application US 2005/0079131, said contrast agent being in the form of an oil-in-water emulsion in which the aqueous continuous phase contains a dispersion of oil droplets (average diameter of approximately 200 nm) incorporating a lipophilic compound coupled to an element with an atomic number>36, said droplets being stabilized with a layer of surfactants, into which an ancillary imaging agent is inserted, the targeting of the biomolecules being provided by DSPE-PEG (2000)-maleimide coupled to a peptidomimetic antagonist of $a_v\beta_3$ integrins.
Figure 5:
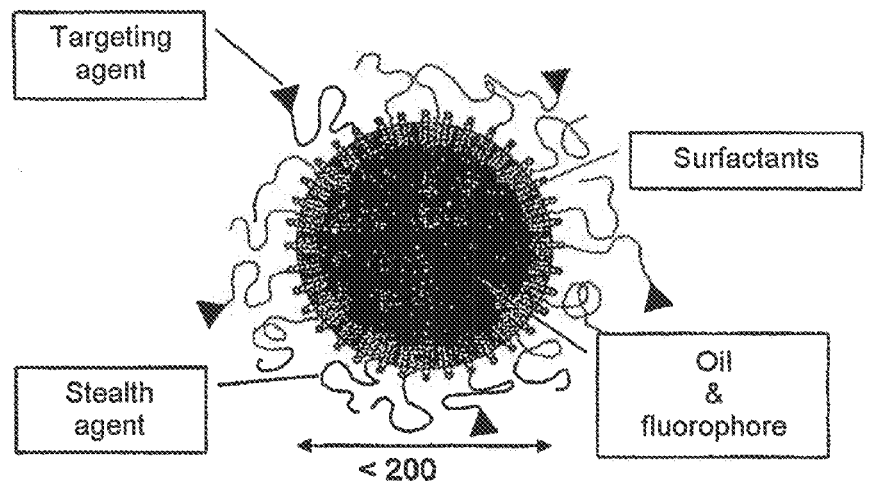
FIG. 5 corresponds to the diagram of the oil-in-water emulsion in accordance with the present invention, in which the aqueous continuous phase contains a dispersion of oil droplets (average diameter<200 nm), at the heart of which at least one lipophilic fluorophore is encapsulated, said droplets being stabilized with a peripheral surfactant layer comprising at least one surfactant, at least one stealth cosurfactant, and at least one agent for targeting a biological activity of interest.
Figure 6:
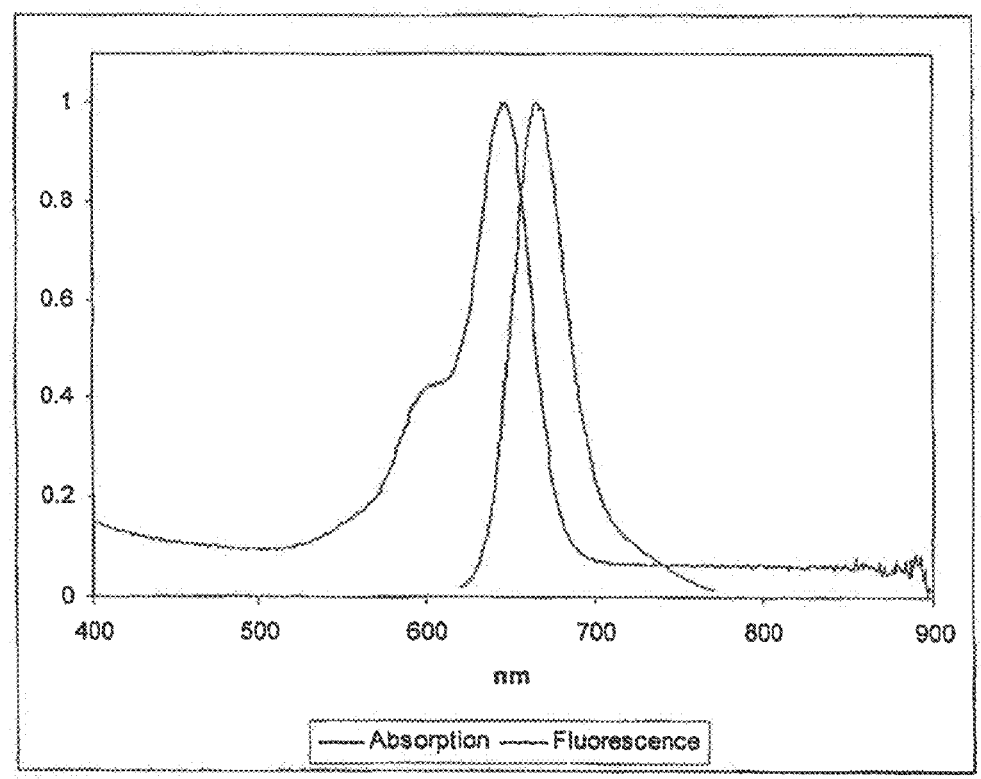
FIG. 6 represents the absorption/emission spectrum of an emulsion in accordance with the present invention in which the oil droplets are made up of soybean oil containing the fluorophore DiD sold under the reference D-307 by the company Invitrogen. In this figure, the intensity expressed in arbitrary units is as a function of the wavelengths expressed in nm, the absorption corresponding to the curve on the left, and the emission of the fluorescence corresponding to the curve slightly shifted to the right.

The absorption and emission spectra for this emulsion are represented in the attached FIG. 6, in which the intensity expressed in arbitrary units is as a function of the wavelength expressed in nm; in this figure, the absorption corresponds to the curve on the left and the emission of the fluorescence corresponds to the curve slightly shifted to the right.

Figure 7:
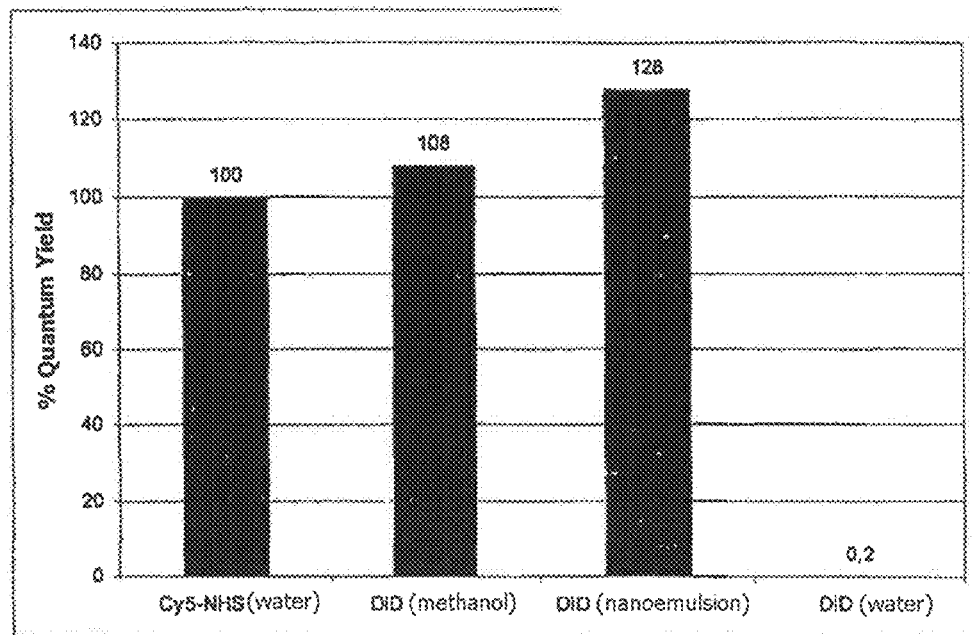
FIG. 7 shows the quantum yields of the DiD fluorophore as a function of its medium (in solution in methanol, incorporated into nanoemulsions and in solution in water) compared with that of Cy5-NHS (Amersham), the value of which was arbitrarily fixed at 100.

The quantum yield of this emulsion is 1.3 times greater than that of Cy5-NHS, as shown in the attached FIG. 7.

Figure 8:
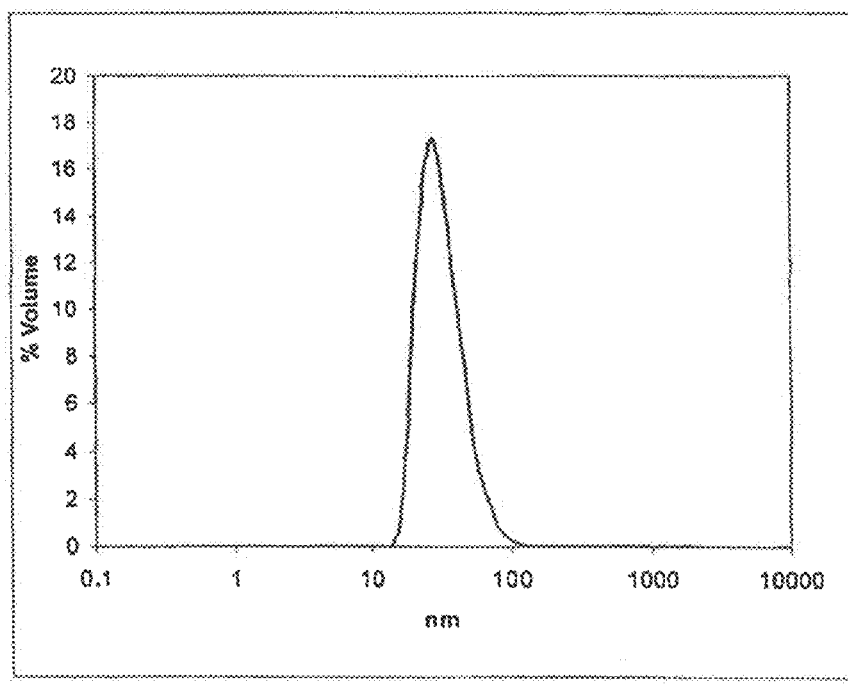
FIG. 8 represents the volume-weighted size distribution of an emulsion of the present invention prepared according to example 1. In this figure the percentage by volume is as a function of the size in nm.

The nominal size of the nanoparticles, determined by dynamic light scattering on a device sold under the reference ALV-5000/EPP by the company ALV, was less than 70 nm. The size distribution curve is represented in attached FIG. 8.

EXAMPLE 2

Preparation of Fluorescent Nanoemulsions Functionalized Before Emulsification 1) Preparation of a Targeting Peptide Functionalized with a Grafting Cosurfactant A cyclic peptide for targeting $\alpha_v\beta_3$ integrins overexpressed at the surface of endothelial cells, c(RGDf[ε-S-acetylthioacetyl])K (identified SEQ ID No. 1 in the attached sequence listing) sold by the company Ansynth Service BV (The Netherlands) and referred to as cRGD in the subsequent text, having a thiol group protected in the form of a mercaptoacetic acid, was coupled to a grafting cosurfactant, distearoylphosphatidylethanolamine poly(ethylene glycol 2000)-maleimide (i.e. the DSPE-PEG (2000)-maleimide) sold by the company Avanti Polar Lipids, Inc.). The latter was mixed with the cRGD with a molar ratio of 1:1 in a (4-(2-hydroxyethyl)-1-piperazineethane sulfonic acid/ethylenediaminetetraacetic acid (HEPES/EDTA) buffer solution with a hydroxylamine concentration of 0.05 M. The solution was stirred slowly under a slight stream of argon at ambient temperature for 4 hours, evaporated under reduced pressure and then redissolved in chloroform with a view to the second step.

2) Preparation of a Premix for the Dispersed Phase

The premix was made up of 15% w/w of soybean oil (Sigma-Aldrich), 45% w/w of SUPPOCIRE®. NC (Gattefosse), 38% w/w of Lecithin LECITHIN® S-75 (Lipoid) and 2% w/w of DSPE-PEG(2000)-maleimide (Aventi Polar Lipids, Inc.) coupled to cRGD. These compounds were dissolved in chloroform, and the solution was then evaporated under reduced pressure and dried at 50° C. so as to obtain a viscous oil that solidifies upon cooling.

3) Preparation of the Dispersed Phase

A 0.833 g sample of the premix prepared above in the second step was taken, at a temperature of approximately 70° C., and 1.5 mg of the fluorophore D-307 (Invitrogen) were then added thereto. The solution was then homogenized by vortex, and maintained at 70° C. in anticipation of the emulsification phase.

4) Preparation of the Continuous Phase

The continuous phase was composed of 0.125 g of glycerol, 0.55 g of MYRJO 53 and a PBS buffer solution to make the weight up to 4.166 g. This solution was heated to 70° C. in anticipation of the emulsification.

5) Emulsification

The continuous phase was added to the dispersed phase and the mixture was then emulsified for 6 minutes for a total energy of 6000 joules with an AV505® sonicator equipped with a conical probe 3 mm in diameter (Sonics, Newtown).

6) Preparation for Intravenous Injection in Mice

The emulsion obtained above was then diluted by a factor of 6.25 with PBS, and then filtered through a 0.22 μm filter so as to remove the aggregates, but also to sterilize it.

This emulsion can then be directly used as a fluorescent probe for in vivo functional imaging.

EXAMPLE 3

Preparation of Fluorescent Nanoemulsions Functionalized after Emulsification 1) Preparation of a Premix for the Dispersed Phase The premix was made up of 15% w/w of soybean oil (Sigma-Aldrich), 45% w/w of SUPPOCIRE® NC (Gattefosse), 38% w/w of soybean lecithin S-75 (Lipoid) and 2% w/w of DSPE-PEG (2000)-maleimide (Aventi Polar Lipids). These compounds were dissolved in chloroform, and the solution was subsequently evaporated under reduced pressure and dried at 50° C. so as to obtain a viscous oil that solidifies upon cooling.

2) Preparation of the Dispersed Phase

A sample of 0.833 g of the premix described above in 1) was taken at a temperature of approximately 70° C., and 1.5 mg of the fluorophore DiD sold under the reference D-307 by the company Invitrogen were added thereto. The solution was homogenized by vortex, and maintained at 70° C. in anticipation of the emulsification phase.

3) Preparation of the Continuous Phase

The continuous phase was composed of 0.125 g of glycerol, 0.55 g of MYRJ® 53 and a PBS buffer solution so as to make the weight up to 4.166 g. This solution was heated to 70° C. in anticipation of the emulsification.

4) Emulsification

The continuous phase was added to the dispersed phase and the mixture was emulsified for 6 minutes for a total energy of 6000 joules with an AV505® sonicator equipped with a conical probe 3 mm in diameter (Sonics, Newtown).

5) Functionalization

The emulsion was diluted in a HEPES/EDTA buffer containing 0.05 M of hydroxylamine. The solution was deoxygenated for 30 minutes with a stream of argon, and then 2 mg of the cRGD peptide bearing a protected thiol group (c(RGDfK(Ac—S—CH.sub.2CO)), Ansynth Service BV, The Netherlands) were added. The reaction mixture was stirred slowly under a light stream of argon at ambient temperature for 4 hours. The solution was then dialyzed against PBS with a SPECTRA/POR® dialysis membrane having a cutoff threshold equal to 12,000 so as to remove the cRGDs that had not reacted.

6) Preparation for Intravenous Injection in Mice

The emulsion obtained above was diluted by a factor of 6.25 with PBS, and then filtered through a 0.22 μm filter so as to remove the aggregates, but also to sterilize it.

This emulsion can then be directly used as a fluorescent probe for in vivo functional imaging, and in particular for tumor detection in mice.

To this effect, 5-to-6-week-old female Nude mice (IFFA-Credo, Marcy l'Etoile, France), kept under pathogen-free conditions, were used as animal model. Ts/Apc cells (murine breast cancer model) were cultured in an RPMI 1640 culture medium containing 10% of fetal calf serum, 50 U/ml of penicillin, 50 μg/ml of streptomycin, and 50 μg/ml of 2-mercaptoethanol at $2.5 \times 10^{-5}$ M (all these products being sold by the company Sigma-Aldrich). The cells were maintained at 37° C. under a humid atmosphere with 5% $CO_2$. $10^6$ cells were subsequently injected subcutaneously into the back of the mice two weeks before injection of the nanoemulsion as prepared above in this example. The injection was carried out intravenously in the tail, in a proportion of 200 μl of solution per mouse. All the injections and image acquisitions were carried out while the mice were kept under general gaseous (isoflurane) anesthesia.

Figure 9:
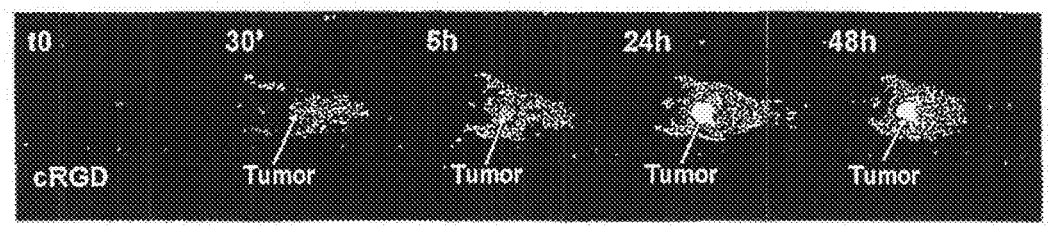
FIG. 9 shows the change in the distribution over time in a mouse bearing a Ts/Apc tumor (breast carcinoma, murine model), of a fluorescent emulsion in accordance with the present invention, i.e. containing the DiD fluorophore and functionalized with cRGDs as described in example 3. The distribution shows a considerable accumulation in the tumor region.

The anesthetized animals were imaged with a fluorescence reflectance imaging (FRI) device comprising, as excitation source, a crown of LEDs equipped with interference filters, emitting at 633 nm (illumination power 50 $\mu W \cdot cm^{-2}$) as described, for example, in the article by I. Texier et al., "*Luminescent probes for optical in vivo imaging*", Proceedings of the SPIE, 2005, 5704, 16-22. The images were collected after filtration by means of an RG665 colored filter of optical density>5 at the excitation wavelength by a CCD camera (Orca BTL, Hamamatsu) with an exposure time of 20 ms. The signals were quantified using image processing software. The images recorded 30 minutes, 5 hours, 24 hours and 48 hours after injection of the nanoemulsion functionalized with cRGD and encapsulating the DiD fluorophore show a gradual accumulation of the fluorescence signal in the tumor over time (FIG. 9). The image t0 of FIG. 9 represents a fluorescence image of the mouse before injection of the nanoemulsion.

EXAMPLE 4

Comparative Biodistribution of Nonfunctionalized Nanoparticles and of a Nonencapsulated Hydrophilic Fluorophore after Intravenous Injection in Mice 200 μl of the emulsion prepared above in example 1 (emulsion using the DiD fluorophore sold by Invitrogen under the reference D-307), corresponding to 10 nmol of fluorophore, were injected intravenously into the tail of 6-to-8-week-old female Nude mice kept under pathogen-free conditions (IFFA-Credo, Marcy l'Etoile, France). The anesthetized animals were imaged with the fluorescence reflectance imaging device described above in example 3.

By way of comparison, 200 μl of a comparative composition containing 20 nmol of a fluorophore Cy5-NHS (Amersham) not in the form of an emulsion, were also injected into mice, under the same conditions as for the emulsion of example 1.

Figure 10:
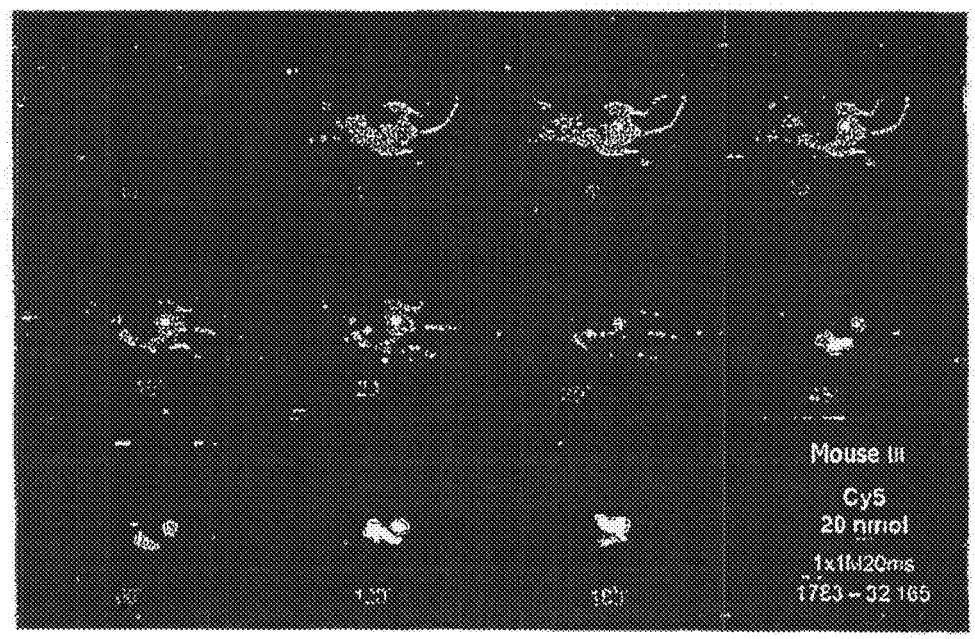
FIG. 10 shows the change in distribution, over time, in mice, of a fluorescent probe which is not part of the invention, i.e. a cyanin Cy5-NHS (Amersham), which is a hydrophilic analog of the DiD fluorophore. The cyanin is not encapsulated in an emulsion and has no targeting agent. The fluorophore is first stored in the kidneys and then eliminated.

The results obtained have been reported in the attached FIG. 10, which shows the change in distribution over time of the Cy5-NHS cyanin (Amersham). It can in particular be seen therein that the kidneys and the bladder rapidly accumulate the fluorophore, limiting the time during which the latter can be imaged in the organism.

Figure 11:
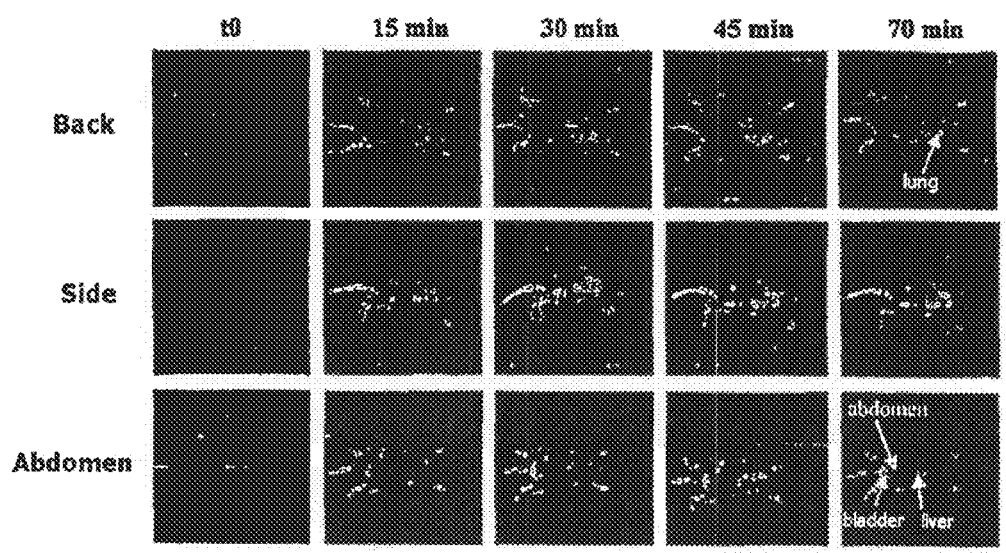
FIG. 11 shows the change in distribution over time in mice, of a fluorescent emulsion in accordance with the present invention, i.e. containing the DiD fluorophore, without targeting agent. The distribution of the nanoparticles in the organism is very homogeneous and there is no elimination.

By way of comparison, the attached FIG. 11 shows the change in distribution of the droplets loaded with DiD fluorophore over time. It can in particular be seen that even though some organs initially take up a considerable part or the fluorophore-loaded droplets (such as the liver and the lungs), the fluorescence becomes homogeneous with time. These results show, therefore, that the encapsulation of the fluorophore within the oil droplets improves the circulation time and reduces its elimination by certain organs such as the intestine, the liver or the kidneys, allowing a better exploration of the whole of the body of the animal.

EXAMPLE 5

Study of the Effect of Encapsulation of a Fluorophore in Lipid Nanoparticles on the Lifetime of the Fluorescence The objective of this example is to demonstrate the effect of the encapsulation of a fluorophore compound in an oily phase on the lifetime of the fluorescence.

To do this, a lipid fluorophore sold by Invitrogen, DiR, was encapsulated in lipid nanoparticles of oil-in-water emulsion type according to the method described above in example 1.

The composition of these nanoemulsions, comprising a lipid core composed of 75% by weight of SUPPOCIRE® NC and 25% by weight of soybean oil, is given in table 1 below:

TABLE 1

Amounts per 5 g of nanoemulsion

| | | Mass (in mg) | % |
|---|---|---|---|
| Dispersed phase | Soybean oil | 125 | 2.5 |
| | SUPPOCIRE ® NC | 375 | 7.5 |
| Surfactants | Lecithin | 350 | 7 |
| | MYRJ ® 53 | 550 | 11 |
| Aqueous phase | Glycerol | 125 | 2.5 |
| | PBS | 3475 | 69.5 |

200 μl of the DiR fluorophore, in solution in DMSO at a concentration of 10 mM, and the lecithin were added to the oil mixture (soybean oil/SUPPOCIRE® NC). The mixture obtained was heated to 50-60° C. The glycerol and the surfactant (MYRJ® 53) were dispersed in the PBS solution. The solution was kept hot (50-60° C.) before emulsification. The aqueous solution was then added to the oil/lecithin mixture. The two-phase solution was then emulsified for five minutes at 40° C. with an AV505® sonicator equipped with a conical probe 3 mm in diameter (Sonics, Newtown) set at 30% maximum power. The emulsions thus obtained had a diameter of 35 nm (measured using a ZETASIZER NANO® machine from Malvern Instruments), and a fluorophore concentration of 400 µM.

By way of comparison, a solution of the DiR fluorophore at 10 mM in methanol was also prepared so as to be able to observe the effect of the encapsulation on the fluorescence lifetime.

The fluorescence decays of the fluorophore free in solution in methanol or encapsulated in the lipid nanoparticles of oil-in-water emulsion type, in suspension in PBS (10 mM, pH 7.3), were measured on a measuring system using a neodymium-vanadate, continuous-wave laser [Millennia Pro, Spectra-Physics, USA], (532 nm, 5 W)-pumped sapphire-titanium laser [Tsunami, Spectra-Physics, USA] (80 MHz, 100 femtoseconds), tunable to a wavelength of 700 nm to 1000 nm. Depending on the operating mode of this device, the laser is injected into a multimode optical fiber, used as excitatory fiber for the sample to be studied. A second (detection) optical fiber collects the fluorescence emitted or the laser scattering via a filtering system. The signal is measured by means of a photomultiplier tube [Hamamatsu, Japan] coupled to a TCSPC counting board [Becker&Hickel, Germany]. The latter is controlled by means of a sampled part (4%) of the laser signal (pulse train) via a rapid photodiode (PD) [Becker&Hickel, Germany] before injection into the optical fiber.

The measurements were carried out using a pulsed excitation wavelength of 740 nm. The fluorescence intensity (in arbitrary units) was measured in order to plot curves reflecting the fluorescence decay (fluorescence intensity (arbitrary units) expressed as a function of time (in ps)); curves not represented.

The fluorescence lifetimes were subsequently obtained using the SPCImage software (Becker Hickl GmbH) by means of an adjustment by one single exponential decay ($X_r^2 = 1.0$) of the curves of fluorescence decay deconvolved with respect to the instrumental response function (FRI). They are given in table 2 below:

TABLE 2

| Lifetime of the DiR fluorophore in solution in methanol (in ps) | Lifetime of the DiR fluorophore in the nanoemulsion (in ps) |
| --- | --- |
| 800 | 1000 |

These results demonstrate that the encapsulation of the fluorophore in a lipid nanoparticle of nanoemulsion type leads to an increase in fluorescence lifetime.

EXAMPLE 6

Study of the Effect of Encapsulation of the DiD Fluorophore in Lipid Nanoparticles on the Quantum Yield of Fluorescence A nanoemulsion having the same composition as that described above in example 1, but with a level of doping with DiD fluorophore sold by Invitrogen of 400 µM, was prepared.

The quantum yield of fluorescence ($\Phi$) is expressed by the following equation: ($\Phi$)=(number of photons emitted)/(number of photons absorbed).

It is common practice to determine a quantum yield relative to that of a reference standard, by the techniques known to those skilled in the art. The quantum yield of this formulation was calculated by comparison with a reference standard sample (Nile Blue perchlorate in ethanol, sold by Invitrogen) having a known quantum yield value equal to 0.27. The same measurements (carried out using a Varian spectrophotometer, model Cary 300 and a Perkin Elmer spectrofluorimeter, model LS 50) and calculations were carried out for a solution of DiD fluorophore in methanol (MeOH).

The results obtained are given in table 3 below:

TABLE 3

| | DiD | |
| --- | --- | --- |
| Fluorophore | In solution in MeOH | Nanoemulsion |
| Max. absorption (nm) | 644 | 647 |
| Emission (nm) | 665 | 666 |
| Quantum yield | 0.29 | 0.39 |

These results demonstrate that the encapsulation of the fluorophore in the core of the oil droplets of an oil-in-water nanoemulsion makes it possible to increase the quantum yield of fluorescence.

EXAMPLE 7

Encapsulation of DiD in Lipid Nanoparticles with Oily Cores Having Various Compositions Various formulations obtained with a level of DiD-doping of 400 µM, but with a lipid core having various compositions, were prepared. The method of preparing these nanoemulsions is similar to that described in example 1, but the composition thereof was modified, as described in tables 4 and 5 below. For each of these formulations, the fluorescence lifetime was calculated according to the method explained above in example 5. The excitation wavelength was 630 nm.

These formulations were also compared with a 400 µM solution of DiD in methanol (formulation A).

TABLE 4

Overall composition of the nanoemulsions
Amounts per 5 g of nanoemulsion

| | | Mass (in mg) | % |
| --- | --- | --- | --- |
| Dispersed phase | Total oil (*) | 500 | 10 |
| Surfactants | Lecithin | 250 | 5 |
| | MYRJ ® 53 | 827.5 | 16.55 |
| Aqueous phase | Glycerol | 125 | 2.5 |
| | PBS | 3297.5 | 65.95 |

(*): corresponds to the total amount of components involved in the dispersed oily phase, which is described in detail in table 5 below.

TABLE 5

Composition of the dispersed oily phase/results

| Formulations | Composition of the dispersed oily phase (in % by weight) (per 5 g of nanoemulsion) | Fluorescence lifetime (ns) |
|---|---|---|
| A | — | 1.15 ± 0.05 |
| B | SUPPOCIRE ® NC 100% | 2.07 ± 0.05 |
| C | Soybean oil/SUPPOCIRE ® NC: 25/75 | 1.97 ± 0.05 |
| D | Soybean oil/SUPPOCIRE ® NC: 75/25 | 2.09 ± 0.05 |
| E | Flax oil/SUPPOCIRE ® NC: 75/25 | 1.97 ± 0.05 |

An increase in the fluorescence lifetime of the DiD is clearly observed in the formulations in nanoemulsion form, this being the case for all the lipid compositions tested.

The invention claimed is:

1. A metastable fluorescent emulsion of oil-in-water type that is stable at pH 7.3, comprising
   at least one aqueous continuous phase and
   at least one oily dispersed phase;
   wherein the dispersed phase comprises droplets of:
      at least one liquid biocompatible oil composed of at least one plant or animal oil and
      at least one crystallizable oil having the following composition:
         $C_8$: 0.1 to 0.9%,
         $C_{10}$: 0.1 to 0.9%,
         $C_{12}$: 25 to 50%,
         $C_{14}$: 10 to 24.9%,
         $C_{16}$: 10 to 24.9%,
         $C_{18}$: 10 to 24.9%,
   wherein said droplets have an average diameter greater than or equal to 10 nm and less than or equal to 200 nm and contain at least one lipophilic fluorophore which absorbs and emits at a wavelength between 640 and 900 nm, and
   wherein said droplets are stabilized by a surfactant layer located at the periphery of said droplets, wherein said layer comprises, as a mixture, at least one amphiphilic surfactant and at least one stealth cosurfactant.

2. The emulsion as claimed in claim 1, wherein the average diameter of the droplets is between 10 and 80 nm, limits included.

3. The emulsion as claimed in claim 1, wherein the plant oil is soybean oil.

4. The emulsion as claimed in claim 1, wherein the ratio by weight of liquid biocompatible oil/crystallizable oil ranges between 10/90 and 90/10, limits included.

5. The emulsion as claimed in claim 1, wherein the amphiphilic surfactants are selected from the group consisting of compounds of which the lipophilic part comprises a linear or branched, saturated or unsaturated chain containing from 8 to 30 carbon atoms.

6. The emulsion as claimed in claim 1, wherein the amphiphilic surfactants are selected from the group consisting of phospholipids, cholesterols, lysolipids, sphingomyelins, tocopherols, glucolipids, stearylamines, cardiolipins of natural or synthetic origin, molecules composed of a fatty acid coupled to a hydrophilic group by an ether or ester function, polymerized lipids, lipids conjugated to short chains of polyethylene oxide (PEG), sugar esters, and mixtures thereof.

7. The emulsion as claimed in claim 6, wherein the amphiphilic surfactants are selected from the group consisting of soybean lecithin, phospholipids and cholesterol.

8. The emulsion as claimed in claim 1, wherein the lipophilic fluorophores are selected from the group consisting of fatty acid analogs, sphingolipids, steroids, lipopolysaccharides and phospholipids functionalized with a group which absorbs and emits between 640 and 900 nm, and amphiphilic derivatives thereof.

9. The emulsion as claimed in claim 8, wherein the fluorophores are amphiphilic derivatives of dialkylcarbocyanines.

10. The emulsion as claimed in claim 1, wherein the stealth cosurfactant(s) is (are) selected from the group consisting of amphiphilic molecule(s) of which the hydrophilic part is completely or partly composed of a polyethylene oxide (PEO) chain in which the number of PEO units ranges from 2 to 500, and polysaccharide(s).

11. The emulsion as claimed in claim 10, wherein the stealth cosurfactant(s) is (are) polyethylene glycol/phosphatidylethanolamine (PEG-PE) conjugated compound(s), fatty acid ether(s) of polyethylene glycol, fatty acid ester(s) of polyethylene glycol, and ethylene oxide/propylene oxide block copolymer(s).

12. The emulsion as claimed in claim 1, wherein the surfactant layer located at the periphery of the droplets also comprises at least one agent for targeting a biological activity of interest, said targeting agent comprising an amphiphilic grafting cosurfactant (CoTA) of which the hydrophilic part is covalently bonded to a biological ligand.

13. The emulsion as claimed in claim 12, wherein said targeting agent is at least one compound of formula (I) below:

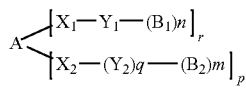 (I)

in which:
A is the lipophilic part of the CoTA,
$X_1$ and $X_2$, which may be identical or different, constitute the hydrophilic part of said CoTA and are composed of a flexible spacer arm that is a saturated or unsaturated, linear or branched carbon-based chain optionally substituted, interrupted and/or terminated with one or more heteroatoms selected from the group consisting of N, O, P and S, and/or with one or more groups selected from the group consisting of $C_1$-$C_4$ alkyl, $C_1$-$C_4$ alkoxy and aryl radicals, or with one or more functional groups selected from the group consisting of ether, ester, amide, carbonyl, carbamate, urea, thiourea and disulfide;
$Y_1$ and $Y_2$, which may be identical or different, are chemical groups capable of linking $X_1$ and $B_1$, and $X_2$ and $B_2$, respectively, by covalent bonds;
$B_1$ and $B_2$, which may be identical or different, are biological ligands, one chemical functional group of which is involved in the covalent bond formed with $X_1$ and $X_2$, respectively;
n is an integer between 1 and 20, limits included;
q is an integer equal to 0 or 1;
m is an integer between 0 and 20, limits included, provided that m=0 when q=0;
p is an integer between 0 and 10, limits included; and
r is an integer between 0 and 10, limits included.

14. The emulsion as claimed in claim 13, wherein the flexible spacer arm is a chain comprising polyoxyethylene or dextran units.

15. The emulsion as claimed in claim 1, wherein the continuous phase of the emulsion is an aqueous phase comprising water and/or a physiologically acceptable buffer or a sodium chloride solution.

16. A diagnostic reagent for diagnosing a biological activity of interest comprising at least one fluorescent emulsion as claimed in claim 1.

17. The reagent as claimed in claim 16, which is an in vivo diagnostic reagent.

18. A method for detecting a biological activity of interest in vivo and/or for development and optimization of a therapeutic tool comprising:
injecting at least one fluorescent emulsion as defined in claim 1 into a human being or into an animal, and
detecting by fluorescence imaging the fluorescent signal emitted by said emulsion.

19. A method for detecting a biological activity of interest in vivo comprising:
injecting at least one fluorescent emulsion as defined in claim 1 into a human being or into an animal, and
detecting by time resolved fluorescence imaging the fluorescent signal emitted by said emulsion.

20. The emulsion as claimed in claim 1, wherein the ratio by weight of liquid biocompatible oil/crystallizable oil ranges between 20/80 and 80/20, limits included.

21. The emulsion as claimed in claim 1, wherein the oily dispersed phase comprises at least 10% by weight of an oil having a viscosity greater than or equal to 100 cP at 20° C.

22. A metastable fluorescent oil-in-water emulsion that is stable at pH 7.3 comprising:
an aqueous continuous phase,
an oily dispersed phase, which contains oil and a lipophilic fluorophore, dispersed in the aqueous continuous phase as droplets having an average diameter ranging from 10 nm to 200 nm; wherein the oil comprises at least one liquid biocompatible oil and at least one crystallizable oil having the following composition $C_8$: 0.1 to 0.9%, $C_{10}$: 0.1 to 0.9%, $C_{12}$: 25 to 50%, $C_{14}$: 10 to 24.9%, $C_{16}$: 10 to 24.9%, and $C_{18}$: 10 to 24.9% at a ratio ranging from 10/90 to 90/10; and wherein the lipophilic fluorophore absorbs and emits light at a near infrared wavelength between 640 and 900 nm; and
an amphiphilic surfactant and a stealth cosurfactant which form a surfactant layer around the periphery of the droplets of the oily dispersed phase.

23. The metastable fluorescent oil-in-water emulsion of claim 22, wherein
the aqueous continuous phase comprises glycerol and phosphate buffered saline (PBS),
the liquid biocompatible oil comprises liquid soybean oil,
the lipophilic fluorophore is 1,1'-dioctadecyl-3,3,3',3'-tetramethylindodicarbocyanin (DiD), the amphiphilic surfactant is lecithin, and
the stealth cosurfactant is polyoxyethylene stearate comprising 50 moles of ethylene oxide.

24. The metastable fluorescent oil-in-water emulsion of claim 22, wherein the oily phase is dispersed in the aqueous continuous phase by sonication or other form of emulsifying.

* * * * *

UNITED STATES PATENT AND TRADEMARK OFFICE
CERTIFICATE OF CORRECTION

PATENT NO. : 9,072,775 B2  Page 1 of 1
APPLICATION NO. : 12/527314
DATED : July 7, 2015
INVENTOR(S) : Mathieu Goutayer et al.

It is certified that error appears in the above-identified patent and that said Letters Patent is hereby corrected as shown below:

On the title page, Item (73), the Assignees' Information has been omitted. Item (73) should read:

--(73) Assignees: COMMISSARIAT A L'ENERGIE ATOMIQUE, Paris (FR);
CENTRE NATIONAL DE LA RECHERCHE SCIENTIFIQUE, Paris (FR);
UNIVERSITE PIERRE ET MARIE CURIE (PARIS 6), Paris (FR)--

Signed and Sealed this
Seventeenth Day of November, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 4
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(4)
<223> OTHER INFORMATION: c(RGDf[e-S-acetyl]thioacetyl})K

<400> SEQUENCE: 1

Arg Gly Asp Leu
1
```